US008010185B2

(12) United States Patent
Ueda

(10) Patent No.: US 8,010,185 B2
(45) Date of Patent: Aug. 30, 2011

(54) METHOD OF DIAGNOSING A LOWER URINARY TRACT DISORDER

(75) Inventor: Tomohiro Ueda, Kyoto (JP)

(73) Assignee: N.M.A. Co., Ltd., Nara (JP)

(*) Notice: Subject to any disclaimer, the term of this patent is extended or adjusted under 35 U.S.C. 154(b) by 789 days.

(21) Appl. No.: 11/945,541

(22) Filed: Nov. 27, 2007

(65) Prior Publication Data

US 2009/0069696 A1    Mar. 12, 2009

(30) Foreign Application Priority Data

Sep. 12, 2007   (JP) .................................. 2007-236093

(51) Int. Cl.
*A61B 6/00* (2006.01)
(52) U.S. Cl. ......... 600/473; 600/476; 600/478; 600/475
(58) Field of Classification Search .................. 600/477, 600/474, 475
See application file for complete search history.

(56) References Cited

U.S. PATENT DOCUMENTS

| | | | | |
|---|---|---|---|---|
| 5,301,688 | A * | 4/1994 | Stephen et al. | 607/99 |
| 6,563,105 | B2 * | 5/2003 | Seibel et al. | 250/208.1 |
| 6,616,653 | B2 * | 9/2003 | Beyar et al. | 606/14 |
| 2005/0038328 | A1 * | 2/2005 | Stoehrer et al. | 600/301 |
| 2007/0260214 | A1 * | 11/2007 | Mikkaichi et al. | 604/500 |

OTHER PUBLICATIONS

Zimmern, P. et al. Fluorescien Angiography of the Bladder: Technique and Relevance to Bladder Cancer and Interstitial Cystitis Patients. Journal of Urology. Jul. 1995; 154(1):62-65.*
Gherghe, Cristian. Narrow-Band Imaging for Diagnosis of Malignant and Premalignant Gastrointestinal Lesions. Journal of Gastrointestinal and Liver Disease. vol. 15, Mar. 2006, p. 77-82.*
"Interstitial Cystitis Diagnosis and Treatment Guideline," *Japanese Society for Scientific Research of Interstitial Cystitis*, pp. 1-94, Jan. 2007.
Nigro, D. A., et al., "Associations Among Cystoscopic and Urodynamic Findings for Women Enrolled in the Interstitial Cystitis Data Base (ICDB) Study," *Urology*, vol. 49, (Supplement 5A), 1997, pp. 86-92.
Waxman, J.A. et al., "Cystoscopic Findings Consistent With Interstitial Cystitis in Normal Women Undergoing Tubal Ligation," *The Journal of Urology*, vol. 160, Nov. 1998, pp. 1663-1667.

* cited by examiner

*Primary Examiner* — Long V. Le
*Assistant Examiner* — Helene Bor
(74) *Attorney, Agent, or Firm* — Price Heneveld LLP

(57) ABSTRACT

A method for sensitively diagnosing lower urinary tract disorders, particularly interstitial cystitis, is provided. The method can visually, simply, and clearly diagnose bladder ulcer without requirement of bladder hydrodistention under anesthesia. In the method, lower urinary tract disorders are diagnosed by observing an abnormality of a blood vessel and/or a newly formed blood vessel in a surface of bladder mucous membrane among abnormalities in blood vessels and/or newly formed blood vessels by visually comparing an image of the surface of the bladder mucous membrane and an image of a deep portion of the bladder mucous membrane obtained using a bladder endoscope system having a narrow band imaging device.

3 Claims, 2 Drawing Sheets

METHOD OF DIAGNOSING A LOWER URINARY TRACT DISORDER

CROSS-REFERENCE TO RELATED APPLICATION

This application claims priority to Japanese Patent Application Serial No. 2007-0236093 entitled METHOD OF DIAGNOSING A LOWER URINARY TRACT DISORDER, filed on Sep. 12, 2007, the entire disclosure of which is incorporated herein by reference.

BACKGROUND OF THE INVENTION

1. Field of the Invention

The present invention relates to a method of diagnosing lower urinary tract diseases, in particular, interstitial cystitis.

2. Description of the Related Art

Lower urinary tract disorders are a generic name for lower urinary tract dysfunctions, and lower urinary tract symptoms, which are caused by lower urinary tract disorders, are classified roughly into three groups: urinary retention symptoms (such as pollakisuria and urinary urgency), urination symptoms (such as decreased urine flow and interrupted urine stream), and post-urination symptoms (such as residual urine feeling and drops after urination). The lower urinary tract symptoms include lower urinary tract pain such as micturition pain, bladder pain, and urethra pain; detrusor overactivity; and dysuria. Furthermore, hematuria is observed in some lower urinary tract disorders. The lower urinary tract disorders are caused by diseases such as interstitial cystitis, prostatic hypertrophy, prostatitis, prostadynia, bladder neck contracture, overactive bladder, and painful bladder syndromes.

Among them, interstitial cystitis causes symptoms such as pollakisuria, excessive urination, urinary urgency, bladder discomfort, and bladder pain and is an intractable disease, though urinary tract infection and other apparent pathosis are not observed. Interstitial cystitis is defined as a disease accompanying non-specific chronic inflammation of bladder, but the cause thereof is not yet clarified. Therefore, the disease is not clearly defined. In addition, interstitial cystitis cannot be cured by conventional antibiotic therapy, unlike common bacterial cystitis.

At present, NIDDK (National Institute of Diabetics and Digestive and Kidney Diseases) is most well known as a diagnosis standard of interstitial cystitis. Japanese Society for Scientific Research of Interstitial Cystitis has published "Interstitial Cystitis Diagnosis and Treatment Guideline" in 2007 and has indicated a clinical diagnosis standard.

In the above-mentioned diagnosis of interstitial cystitis, abnormalities of bladder surface (epithelium) are one of important grounds of the diagnosis. Therefore, it is necessary to observe (1) a bladder ulcer or (2) a petechial hemorrhage caused by bladder hydrodistention under anesthesia. The bladder ulcer is observed by cystoscopy, but only about 10 to 50% of ulcers can be found by conventional endoscopic findings of bladder using visible light (referred to, for example, Nigro, D. A., et al., *Urology*, 1997, 49 (Supplement 5A), pp. 86-92, and Waxman, J. A., et al., *The Journal Of Urology*, Vol. 160, November 1998, pp. 1663-1667). Such a low sensitivity is a large problem for the examination requiring a high sensitivity.

That is, in the conventional findings using visible light, only obvious ulcers such as Hunner's ulcer can be detected. Urologists may think ulcers as that bladder mucous membrane is merely red and may overlook many abnormalities. In other words, though an ulcer is aggregation of blood vessels newly formed in a surface of the bladder, conventional cystoscopy detects blood vessels newly formed in a surface and also blood vessels newly formed in a deep portion of the bladder as red images and cannot or hardly differentiate between the two.

In the diagnosis by bladder hydrodistention under anesthesia, a subject has to stay in a hospital and general anesthesia including lumbar spinal anesthesia is necessary for the hydrodistention. Furthermore, the subject has a pain after the treatment. Thus, physical, mental, and economic burdens of the subject are enormous. In addition, burdens of a person who conducts the diagnosis are similarly enormous and stressful.

Consequently, though a large number of people, particularly middle-aged women, suffer from symptoms of interstitial cystitis, many of them cannot receive diagnosis or are not correctly diagnosed. Consequently, they are still compelled to suffer from the symptoms.

SUMMARY OF THE INVENTION

Accordingly, it is an object of the present invention to provide a method of diagnosing lower urinary tract diseases, particularly interstitial cystitis, with a high sensitivity. The method can visually, simply, and clearly diagnose a bladder ulcer without requirement of bladder hydrodistention under anesthesia.

The present inventors have conducted intensive studies in order to solve the above-mentioned problems and, as a result, have found that angiogenic factors such as platelet-derived endothelial cell growth factor (PD-ECGF) are highly expressed in a mucous membrane layer at an ulcer lesion of interstitial cystitis and that angiogenesis is closely related to ulcers. If the degree of angiogenesis can be examined with a high sensitivity by cystoscopy, a novel method of diagnosing interstitial cystitis can be provided. The present inventors have further found that a bladder endoscope system using specific light, which is limitedly used for detection of cancer at present, is useful as a sensitive method of detecting angiogenesis in bladder mucous membrane surfaces in lower urinary tract diseases such as interstitial cystitis, painful bladder syndrome, and chronic prostatitis. The present invention has been thus completed.

That is, in order to achieve the above-mentioned object, the method of diagnosing a lower urinary tract disorder according to the present invention includes observing a blood vessel and/or a newly formed blood vessel in a surface of bladder mucous membrane using a bladder endoscope system having a specific light observation device.

The specific light observation device is preferably a narrow band imaging (NBI) system, an auto fluorescence imaging (AFI) system, or an infra-red imaging (IRI) system.

Furthermore, in the observation of a blood vessel and/or a newly formed blood vessel in a surface of bladder mucous membrane, it is preferable that an image of a surface of bladder mucous membrane and an image of a deep portion of the bladder mucous membrane that are obtained using a bladder endoscope system having a narrow band imaging (NBI) device be visually compared, and thereby the abnormality of the blood vessel and/or the newly formed blood vessel in the surface of the bladder mucous membrane, among abnormalities in blood vessels and/or newly formed blood vessels, can be observed.

The lower urinary tract disorder is preferably interstitial cystitis.

A bladder endoscope is a medical device for observing inside the bladder of a human body and has a long and narrow shape with a built-in optical system. An image of the inside can be obtained and, at the same time, can be observed by inserting the distal end into a body. Furthermore, some of existing bladder endoscopes can be used for a certain level of operation or sampling. Recently, early detection of a small lesion and observation of small hypertrophy of mucous membrane and deep blood vessels are possible due to the development of specific light and image processing technologies. Methods of specific light observation, for example, narrow band imaging (NBI), auto fluorescence imaging (AFI), and infra-red imaging (IRI), are becoming commercially available. The NBI is available by incorporating a filter and a processor into a conventional bladder endoscope system. An available example of the system is an electronic endoscope system manufactured by Olympus Medical Systems Corp. under the trade name "EVIS LUCERA SPECTRUM" (registered trademark) for early detection of cancer.

In the NBI system, a light beam passed through a filter so as to have a wavelength selected from the range of 400 to 430 nm, preferably, 410 to 420 nm and particularly preferably a wavelength of 415 nm and a light beam passed through a filter so as to have a wavelength selected from the range of 520 to 560 nm, preferably, 530 to 550 nm and particularly preferably a wavelength of 540 nm are used as illumination light of the endoscope. Since both light beams having such wavelengths are highly absorbed by hemoglobin, capillaries can be isolated as black images. The light beam of 415 nm is used for observing a surface of mucous membrane and the light beam of 540 nm is for a moderately deep portion. Since the NBI system can enhance the contrast of swelling against the surrounding tissues to clearly show it, a very small tumor that tends to be overlooked with conventional endoscopes can be found and the boundary of the tumor is also very clear, compared to those found in other methods. In a case of carcinoma in situ (CIS) of the bladder, irregularity of mucous membrane and a flare are emphasized to further clarify the boundary with normal mucous membrane. Consequently, the NBI system is very useful for determining the location for biopsy. In addition, the NBI system is available by incorporating a filter and a processor into a conventional bladder endoscope system and can be changed from usual endoscopy using visible light within one to two seconds with a handy switch of the endoscope.

Conventional endoscopy of interstitial cystitis using visible light can diagnose only obvious ulcers such as Hunner's ulcer. However, the bladder endoscope using the NBI system can detect a change of a mucous membrane layer in the pre-ulcer or the early stage of ulcer as an image of angiogenesis. In addition, in a case of Hunner's ulcer, a lesion at the periphery of the ulcer can also be diagnosed by observing the angiogenic lesion. Therefore, the bladder endoscope using the NBI system is useful for determining an area that should be irradiated with laser in laser cautery of the ulcer.

That is, in the cystoscopy using the NBI, angiogenesis in a surface of mucous membrane, which is characteristic to interstitial cystitis, can be observed by using a light beam having a wavelength of 415 nm, and bladder carcinoma can be diagnosed by observing angiogenesis present in a relatively deep portion of mucous membrane using a light beam having a wavelength of 540 nm. Thus, cancer and interstitial cystitis are clearly distinguished from each other and are diagnosed by observing angiogenesis at each portion of a mucous membrane layer using light having the respective assigned wavelength.

The above-described method enables to diagnose interstitial cystitis in diseases having a lower urinary tract disorder that is diagnosed to be prostatitis, prostatic hypertrophy, prostadynia, prostatic cystitis, prostatic tumor, congestion or hemorrhage in the prostate, or prostatic atrophy; a lower urinary tract disorder that is diagnosed to be bladder neck contracture, bladder neck obstruction, vesicointestinal fistula, or diverticulum of the bladder; a lower urinary tract disorder that is diagnosed to be acute cystitis, chronic cystitis, interstitial cystitis, cystitis trigoni, radiation cystitis, cystitis caused by cancer chemotherapy, or tuberculous cystitis; and a lower urinary tract disorder that is diagnosed to be painful bladder syndrome pollakisuria, frequency urgency syndrome, overactive bladder syndrome, chronic pelvic pain syndrome, aseptic cystitis, or nervous (psychogenic) pollakisuria. As described above, the cause of interstitial cystitis is not yet clarified and thereby the disease is not clearly defined. The US national Institute of Health and other institutes recently use the term "painful bladder syndrome/interstitial cystitis" in some cases. The disorders defined by such a concept are included in the term "interstitial cystitis" used in this description.

Furthermore, the auto fluorescence imaging (AFI) and the infra-red imaging (IRI) can visually distinguish a lesion from normal tissues as in the NBI and are useful as sensitive methods of detecting angiogenesis in a surface of bladder mucous membrane in lower urinary tract diseases such as interstitial cystitis, painful bladder syndrome, and chronic prostatitis.

DETAILED DESCRIPTION OF THE PREFERRED EMBODIMENTS

Diagnosis is carried out by using light beams passed through filters so as to have wavelengths of 415 nm and 540 nm as illumination light of a bladder endoscope. Since both light beams having such wavelengths are highly absorbed by hemoglobin, capillaries can be isolated as black images. The light of 415 nm is used for observing a surface of mucous membrane and the light of 540 nm is for a moderately deep portion. Interstitial cystitis is diagnosed by the presence of a blood vessel image observed using the light having a wavelength of 415 nm.

Angiogenesis in a surface of mucous membrane, which is characteristic to interstitial cystitis, can be observed by the NBI system using light having a wavelength of 415 nm as an image with a color tone different from that of blood vessels in a moderately deep portion of the mucous membrane layer observed using light having a wavelength of 540 nm. In the NBI system, the contrast of a portion where angiogenesis is active under observation using light of 415 nm is enhanced against the surrounding tissues to clearly show the portion. Consequently, an angiogenesis portion that tends to be overlooked by conventional endoscopes can be found and the boundary with normal portions is very clear, compared to those found in other methods.

EXAMPLES

The present invention will now be described further specifically with reference to the examples, but the scope of the invention is not limited to the following examples.

Six subjects diagnosed to be suffering from ulcer interstitial cystitis and having an average age of 64 years were subjected to bladder endoscopy. The six subjects had symptoms in the O'Leary and Sant questionnaire. The ulcer lesions of bladder mucous membrane were observed with conventional bladder endoscopy under spinal anesthesia and then observed with the NBI system.

Figure 1A:
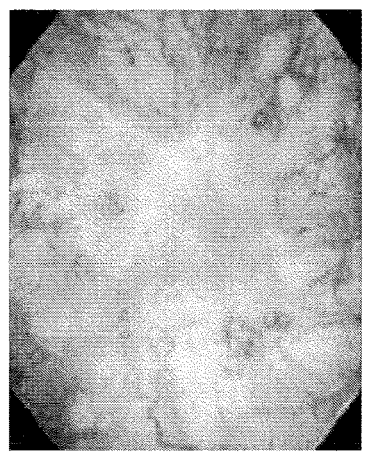
FIG. 1A is a photograph of a bladder mucous membrane of human subject No. 1 using a conventional bladder endoscope using visible light.
Figure 1B:
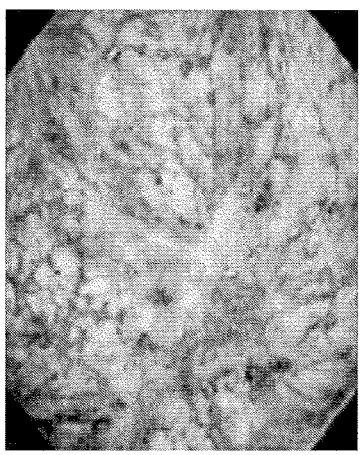
FIG. 1B is a photograph of the bladder mucous membrane shown in FIG. 1A using the NBI system using light of 415 nm.
Figure 2A:
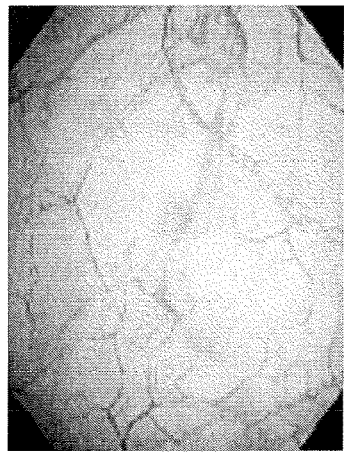
FIG. 2A is a photograph of a bladder mucous membrane of human subject No. 2 using a conventional bladder endoscope using visible light.
Figure 2B:
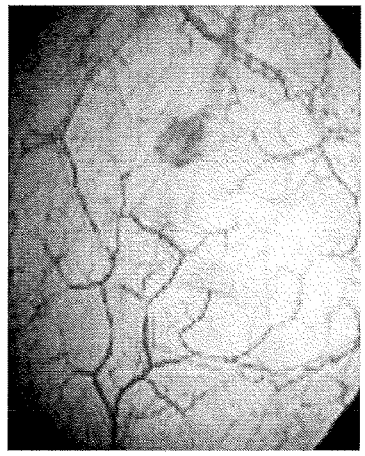
FIG. 2B is a photograph of the bladder mucous membrane shown in FIG. 2A using the NBI system using light of 415 nm.
Figure 3A:
FIG. 3A is a photograph of a bladder mucous membrane of human subject No. 3 using a conventional bladder endoscope using visible light.
Figure 3B:
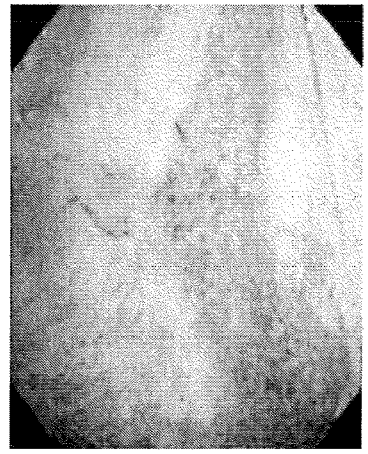
FIG. 3B is a photograph of the bladder mucous membrane shown in FIG. 3A using the NBI system using light of 415 nm.
Figure 4A:
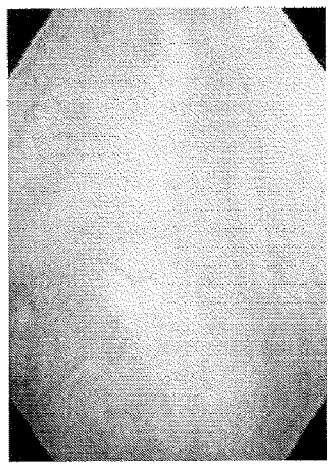
FIG. 4A is a photograph of a bladder mucous membrane of human subject No. 4 using a conventional bladder endoscope using visible light.
Figure 4B:
FIG. 4B is a photograph of the bladder mucous membrane shown in FIG. 4A using the NBI system using light of 415 nm.
Figure 5A:
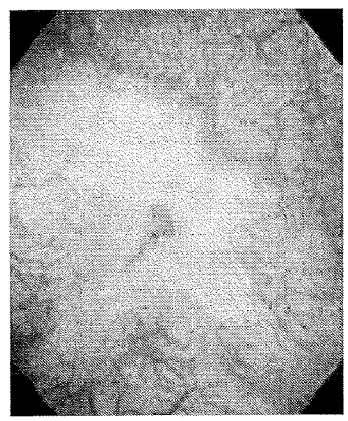
FIG. 5A is a photograph of a bladder mucous membrane of human subject No. 5 using a conventional bladder endoscope using visible light.
Figure 5B:
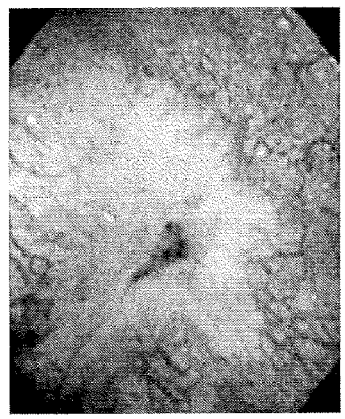
FIG. 5B is a photograph of the bladder mucous membrane shown in FIG. 5A using the NBI system using light of 415 nm.
Figure 6A:
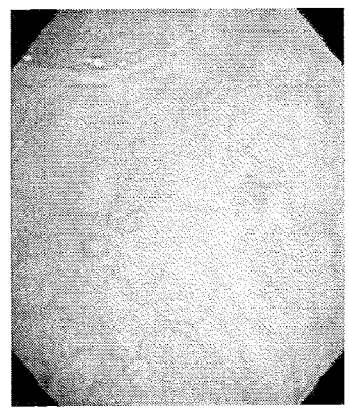
FIG. 6A is a photograph of a bladder mucous membrane of human subject No. 6 using a conventional bladder endoscope using visible light.
Figure 6B:
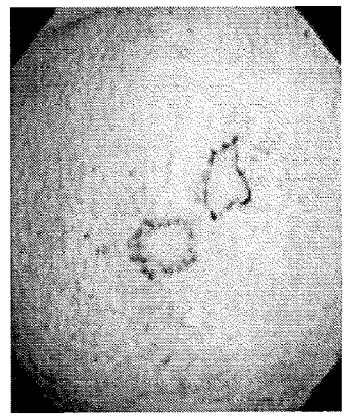
FIG. 6B is a photograph of the bladder mucous membrane shown in FIG. 6A using the NBI system using light of 415 nm.

FIGS. 1A through 6B are photographs of the ulcer lesions of the above-mentioned subjects suffering from ulcer interstitial cystitis taken with the conventional bladder endoscope using usual visible light (FIGS. 1A, 2A, 3A, 4A, 5A and 6A) and taken with the NBI system using light of 415 nm (FIGS. 1B, 2B, 3B, 4B, 5B and 6B). The photographs taken with the NBI system clearly show angiogenic lesions and ulcer lesions.

In other words, in the photographs which were taken with the conventional cystoscope using visible light, blood vessels newly formed in the surfaces and also blood vessels newly formed in the deep portions of bladder mucous membrane are both observed as red images and are difficult to be distinguished.

On the other hand, in the photographs which were taken with the NBI system, blood vessels in the surfaces of mucous membrane, corresponding to ulcer lesions are observed as light blown (or brown) images. These images are clearly differentiated from blue images of blood vessels formed in the deep portions of the mucous membrane. Therefore, abnormality of blood vessels newly formed in a surface of the bladder can be visually and clearly diagnosed without observing petechial hemorrhage by bladder hydrodistention under anesthesia.

What is claimed is:

1. A method of diagnosing a lower urinary tract disorder selected from interstitial cystitis and chronic prostatitis, comprising:
   observing a blood vessel and/or newly formed blood vessel in a surface of a bladder mucous membrane,
   wherein the observation of the blood vessel and/or the newly formed blood vessel in the surface of the bladder mucous membrane includes observing an abnormality in the blood vessel and/or the newly formed blood vessel in the surface of the bladder mucous membrane from among observable abnormalities in the blood vessels and/or the newly formed blood vessels by comparing an image of the surface of the bladder mucous membrane and an image of a deep portion of the bladder mucous membrane obtained using a bladder endoscope system having a specific light observation device.

2. The method according to claim 1, utilizing a narrow band imaging system, an auto fluorescence imaging system, or an infra-red imaging system as the specific light observation device.

3. The method according to claim 1, utilizing the endoscope system to diagnose interstitial cystitis.

* * * * *